(12) United States Patent
Anderson et al.

(10) Patent No.: US 8,309,007 B2
(45) Date of Patent: Nov. 13, 2012

(54) FOLDING APPARATUS AND METHODS FOR BIFURCATION POST-DILATATION BALLOON

(75) Inventors: James Anderson, Fridley, MN (US); Karl Jagger, Deephaven, MN (US); Jan Weber, Maastricht (NL)

(73) Assignee: Boston Scientific Scimed, Inc., Maple Grove, MN (US)

(*) Notice: Subject to any disclaimer, the term of this patent is extended or adjusted under 35 U.S.C. 154(b) by 489 days.

(21) Appl. No.: 12/184,857

(22) Filed: Aug. 1, 2008

(65) Prior Publication Data
US 2010/0030143 A1 Feb. 4, 2010

(51) Int. Cl.
*B29C 53/08* (2006.01)
(52) U.S. Cl. ............ 264/296; 264/294
(58) Field of Classification Search .......... None
See application file for complete search history.

(56) References Cited

U.S. PATENT DOCUMENTS

| | | | |
|---|---|---|---|
| 6,126,652 A * | 10/2000 | McLeod et al. ........ 606/1 |
| 6,146,356 A | 11/2000 | Wang et al. | |
| 6,210,429 B1 | 4/2001 | Vardi et al. | |
| 6,325,826 B1 | 12/2001 | Vardi et al. | |
| 6,692,483 B2 | 2/2004 | Vardi et al. | |
| 6,706,062 B2 | 3/2004 | Vardi et al. | |
| 6,764,504 B2 * | 7/2004 | Wang et al. ........ 623/1.11 |
| 6,988,881 B2 * | 1/2006 | Motsenbocker et al. ..... 425/392 |
| 7,220,275 B2 | 5/2007 | Davidson et al. | |
| 2002/0120320 A1 | 8/2002 | Wang et al. | |
| 2004/0176837 A1 | 9/2004 | Atladottir et al. | |
| 2004/0215227 A1 | 10/2004 | McMorrow et al. | |
| 2005/0244533 A1 | 11/2005 | Motsenbocker et al. | |
| 2007/0203562 A1 | 8/2007 | Malewicz et al. | |
| 2008/0065188 A1 | 3/2008 | Pallazza | |

FOREIGN PATENT DOCUMENTS

| | | |
|---|---|---|
| EP | 0347023 | 12/1989 |
| WO | 0078249 | 12/2000 |
| WO | 2005118046 | 12/2005 |
| WO | 2006113838 | 10/2006 |
| WO | 2007055732 | 5/2007 |

* cited by examiner

*Primary Examiner* — Monica A Huson
(74) *Attorney, Agent, or Firm* — Seager, Tufte & Wickhem, LLC

(57) ABSTRACT

A post dilatation balloon catheter includes a balloon member having a proximal portion, a distal portion and a circumferential bulge portion. The circumferential bulge portion extends around a circumference of the balloon member and is positioned at a location between the proximal and distal portions of the balloon member. The circumferential bulge portion inflates to a maximum inflated dimension that is greater than a maximum dimension of the proximal and distal portions of the balloon member. The balloon member is arranged into a folded state by folding at least one of the distal and proximal portions of the balloon member in a separate step from folding the circumferential bulge portion.

15 Claims, 9 Drawing Sheets

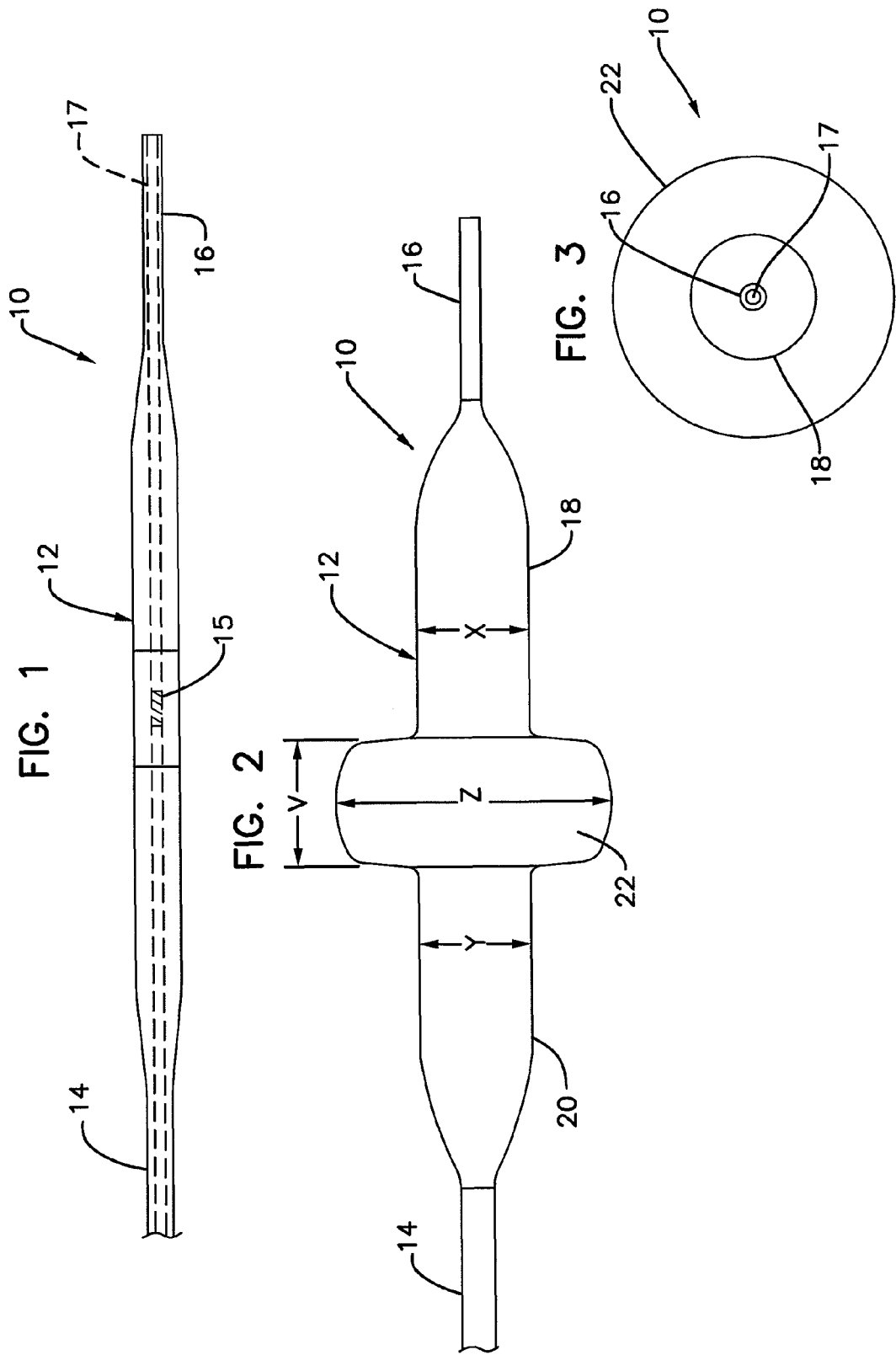

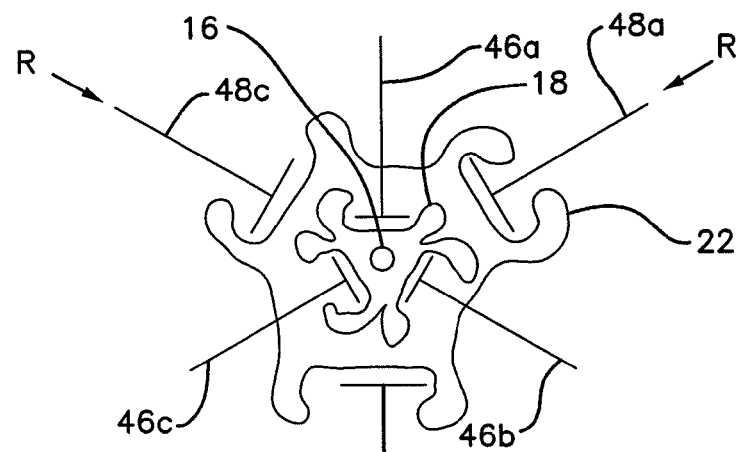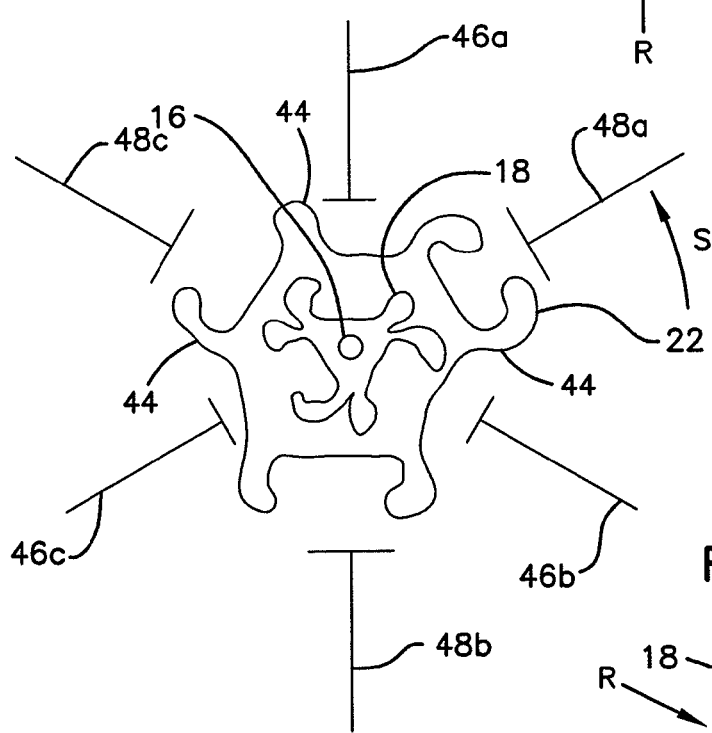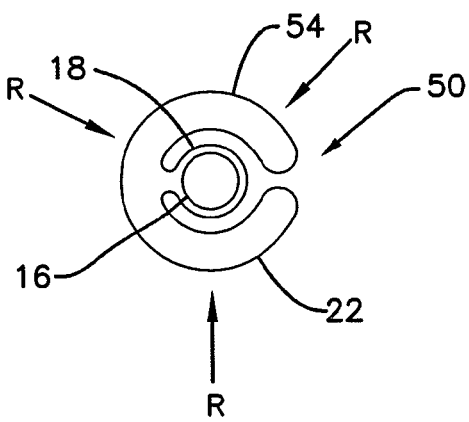

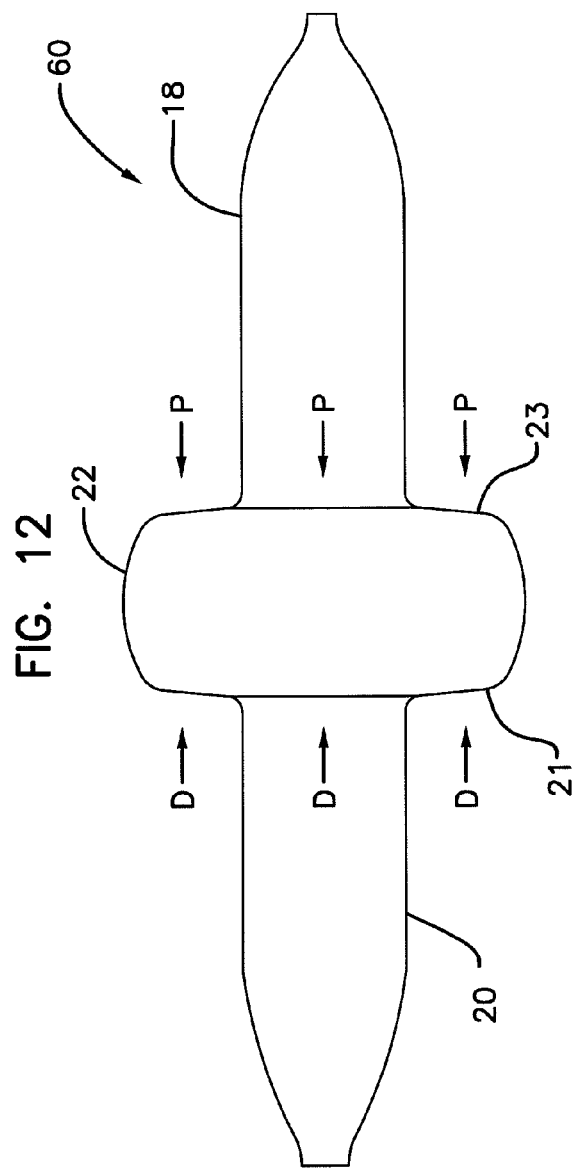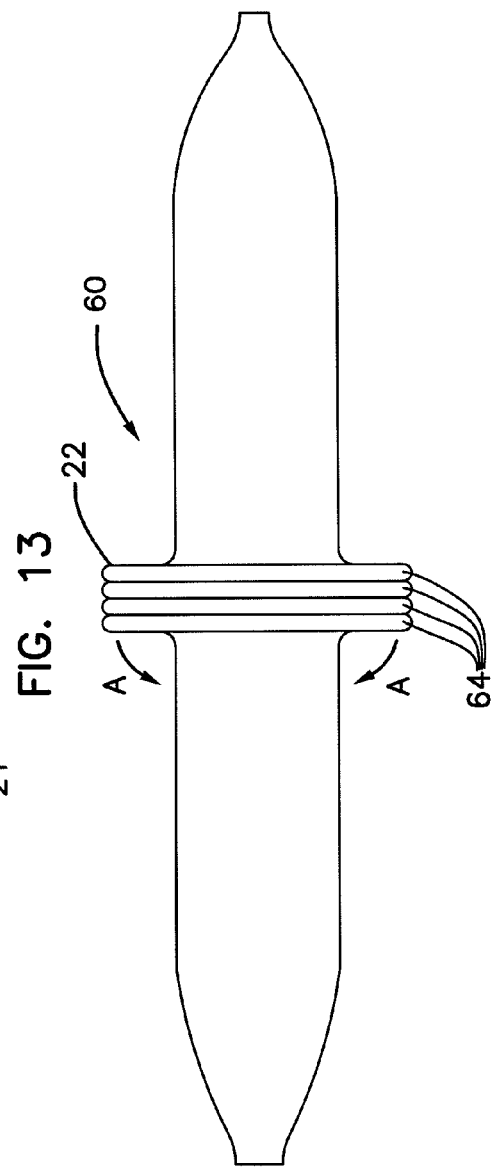

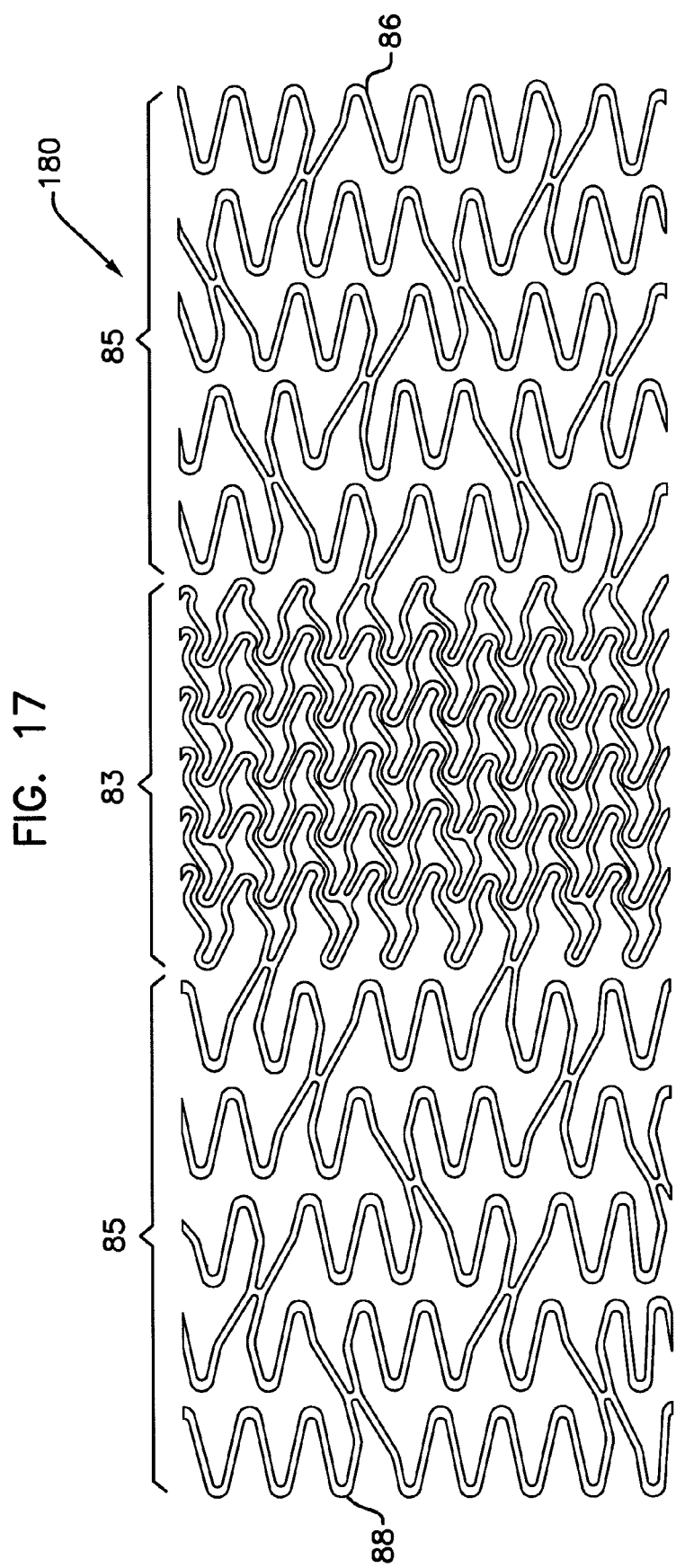

FOLDING APPARATUS AND METHODS FOR BIFURCATION POST-DILATATION BALLOON

TECHNICAL FIELD

This disclosure generally relates to catheter assemblies, and more particularly relates to post-dilatation balloons for treatment of vessel bifurcations and related balloon folding methods.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed.

SUMMARY OF THE DISCLOSURE

The present disclosure generally relates to post-dilatation balloons use to treat vessel bifurcations. One aspect relates to a post-dilatation balloon that generally includes a distal portion, a proximal portion, and a circumferential bulge portion. The circumferential bulge portion extends around a circumference of the balloon member and is positioned at a location between the proximal and distal portions of the balloon member. The circumferential bulge portion inflates to a maximum inflated dimension that is greater than a maximum inflated dimension of the proximal and distal portions of the balloon restricting member.

Another aspect relates to methods of folding a post-dilatation balloon having a circumferential bulge portion and at least one of a proximal portion and a distal portion that has a maximum inflated dimension that is less than a maximum inflated dimension of the circumferential bulge portion. The method includes folding the proximal or distal portion of the balloon in a separate step from folding the circumferential bulge portion of the balloon. Various folding techniques and fold configurations are possible for each of the proximal and distal portions and the circumferential bulge portion.

There is no requirement that an arrangement or method include all features characterized herein to obtain some advantage according to this disclosure.

BRIEF DESCRIPTION OF THE DRAWINGS

FIG. 1 is a schematic side view of an example balloon catheter in accordance with principals of the present disclosure, wherein the balloon of the balloon catheter is in an uninflated state.

FIG. 2 is a schematic side view of the balloon catheter shown in FIG. 1 with the balloon in an inflated state.

FIG. 3 is a schematic front view of the balloon catheter shown in FIG. 2.

FIG. 9 is a schematic front view of the balloon catheter shown in FIG. 8A with a second set of folding members arranged in engagement with the circumferential bulge portion of the balloon.

FIG. 10 is a schematic front view of the balloon catheter shown in FIG. 9 with the distal portion of the balloon having three U-shaped folds and the circumferential bulge portion having three U-shaped folds.

FIG. 11 is a schematic end view of the balloon catheter shown in FIG. 2 with the distal portion and the circumferential bulge portion each folded in a C-shaped fold configuration.

FIG. 12 is a schematic side view of the balloon catheter shown in FIG. 2 with the circumferential bulge portion having an axially applied compression force being applied.

FIG. 13 is a schematic end view of the balloon catheter shown in FIG. 12 with the circumferential bulge portion compressed axially into a plurality of parallel arranged folds.

FIG. 17 is a side view of an example stent construction in accordance with principles of the present disclosure.

DETAILED DESCRIPTION

Figure 4:
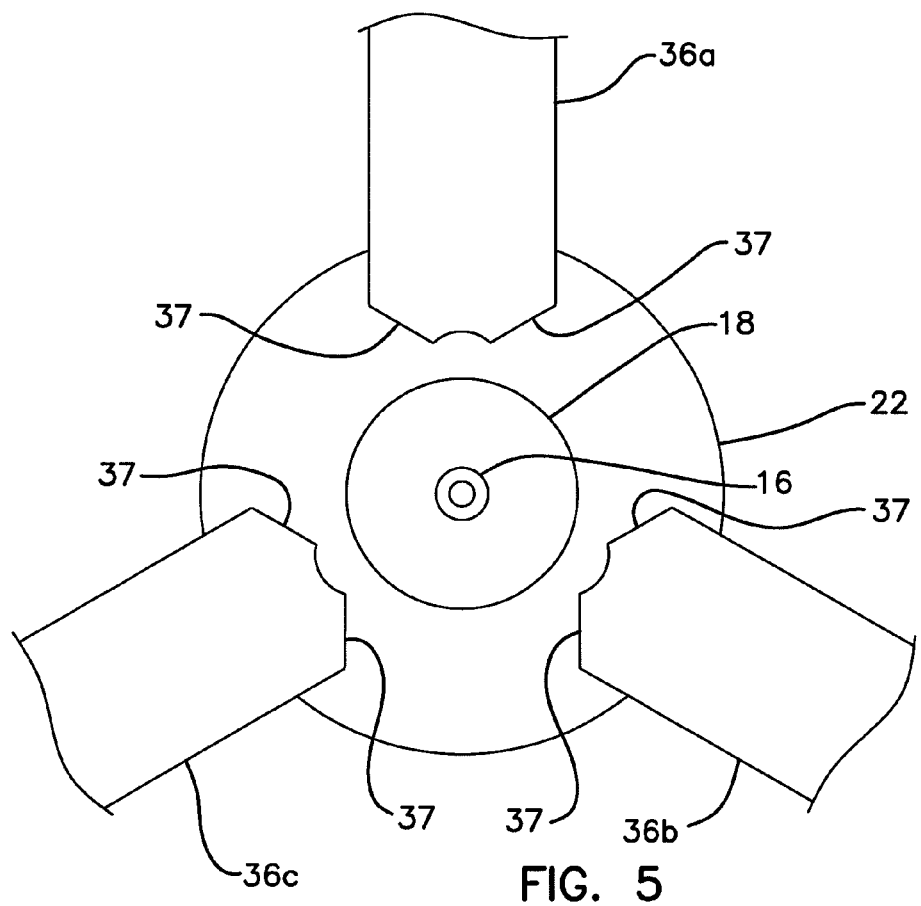
FIG. 4 is a schematic front view of the balloon catheter shown in FIG. 2 with a first set of folding members arranged to compress a distal portion of the balloon.
Figure 5:
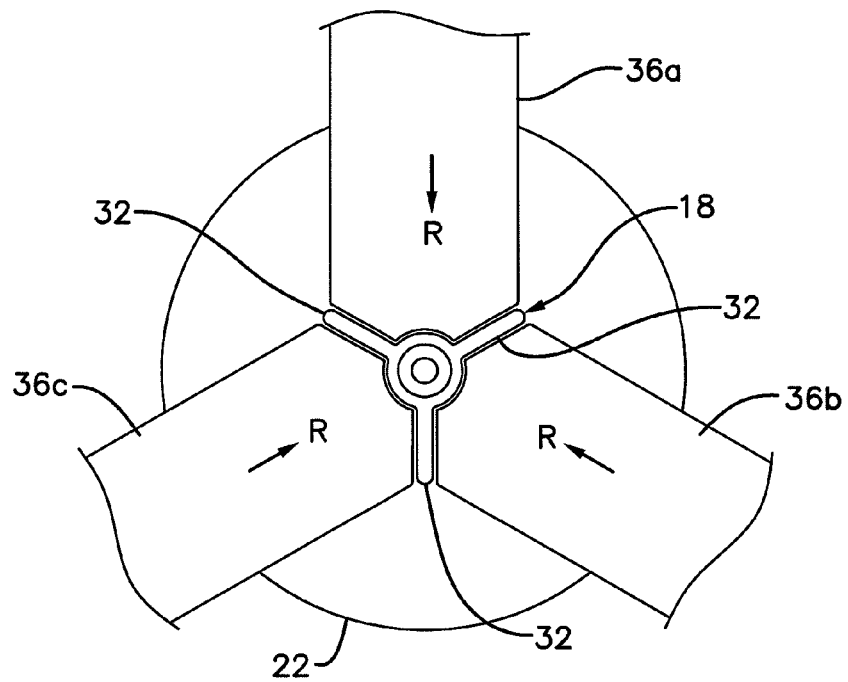
FIG. 5 is a schematic front view of the balloon catheter shown in FIG. 2 with the first set of folding members having compressed the distal portion of the balloon into three wing folds.

This disclosure relates to bifurcation treatment systems, catheter assemblies, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems. The catheter assemblies, systems and methods disclosed herein can be used for locating a branch vessel of the vessel bifurcation and for placement of a stent relative to the vessel bifurcation for treatment of the vessel bifurcation.

One way of treating a vessel bifurcation is to place a conventional stent in the main vessel of the vessel bifurcation and extend some of the struts of the stent as far as possible into the branch vessel of the vessel bifurcation. Some stent designs such as the stent construction shown in FIG. 17 include a plurality of longer free strut structures in a center section of the stent. These longer free strut structures are able to extend further into the branch vessel as compared to struts at distal and proximal end portions of the stent.

Even with such new stent designs, the stent structure that protrudes into the branch vessel from within the main vessel typically requires an additional balloon to move the stent structure into the branch vessel. One such balloon construction is a "submarine" type balloon that includes a bulge portion positioned at a particular circumferential location along a length main balloon. The bulge portion must be aligned both radially and axially with the opening into the branch vessel. Inflation of the bulge portion when so aligned can help extend the stent struts into the branch vessel. The level of precise axial and radial alignment typically necessary for use of such submarine balloons can cause some difficulty in properly treating the vessel bifurcation.

Another option for extending the stent structure into the branch vessel is to use a balloon having an inflated diameter that is greater than the internal diameter of the main vessel. Inflation of such a balloon can cause the stent to bulge or otherwise expand into the branch vessel. However, the enlarged size of the balloon can cause undesired stress in those portions of the main vessel that are proximal and distal of the opening into the branch vessel.

The following description with reference to the attached figures describe various balloon catheter arrangements that provide bulging of the stent structure into the branch vessel without imposing undo stress in the main vessel wall at locations distal and proximal of the opening into the branch vessel, or undo stress in the main vessel wall opposite the opening into the branch vessel. Furthermore, the balloon arrangements described with greater detail below with reference to the figures can provide extension of the stent structure into the branch vessel without the need for radial positioning of any feature of the balloon relative to the opening into the branch vessel as long as a specified portion of the balloon is arranged axially aligned with the opening into the branch vessel.

One feature common to some of the catheter assemblies described herein is a circumferentially arranged bulge portion of the balloon that extends further radially than proximal and distal portions of the balloon extend radially. This bulge portion typically extends around an entire circumference of the balloon member. In some arrangements, the bulge portion can extend less than completely around the entire circumference of the balloon member while still extending around substantially all of the circumference of the balloon member.

The bulge portion of the balloon can be formed in various ways using a variety of structures. Folding of the bulge portion in preparation for advancing the balloon of the balloon catheter to the vessel bifurcation can be performed concurrently or sequentially relative to folding of proximal and distal portions of the balloon. Some of the example folding methods described herein are directed to a two-step folding process in which at least one of the proximal and distal portions of the balloon is first folded, followed by folding of the bulge portion.

The example balloon catheters shown and described with reference to the attached figures are typically referred to as post dilatation balloon catheters. A post dilatation device is typically used after a stent has already been expanded into engagement with a vessel. In the case of treating a vessel bifurcation, a post dilatation balloon catheter can be used to further expand portions of a stent that has already been expanded into engagement with the main vessel at the vessel bifurcation. The stent is usually positioned spanning the opening into a branch vessel of the vessel bifurcation. In some arrangements, the post dilatation balloon can expand portions of the stent into the branch vessel.

An example catheter assembly 10 shown with reference to FIGS. 1-3 includes a balloon member 12, a shaft 14, and a guidewire housing 16 defining a guidewire lumen 17. The balloon 12 is positioned extending from a distal end of the shaft 14. The guidewire housing 16 extends through at least a portion of the shaft 14, through the balloon member 12, and extends distally of the balloon member 12.

The balloon member 12 includes a distal portion 18, a proximal portion 20, and a circumferential bulge portion 22. The distal portion 18 has a distal maximum inflation dimension X, the proximal portion 20 has a proximal maximum inflation dimension Y, and the circumferential bulge portion has a maximum inflation dimension Z when inflated (see FIG. 2). The circumferential bulge portion 22 can have a constant diameter along a length V that is the maximum inflation dimension Z. Alternatively, the diameter of the circumferential bulge portion 22 can be variable along the length V. Typically, a minimum dimension of the circumferential bulge portion 22 is greater than the dimensions X, Y.

The balloon member 12 can be folded when in a deflated state in preparation for advancing the balloon catheter 10 within a patient to a vessel bifurcation treatment site. Typically, the balloon member 12 is deflated as part of the folding process. In some arrangements, the act of folding the balloon causes the balloon member 12 to at least partially deflate.

Providing certain balloon folding arrangements for the balloon member 12 can help minimize the outer profile of the balloon catheter 10 and provide predetermined movement of the balloon member 12 relative to a vessel bifurcation as the balloon member is inflated.

The distal and proximal portions 18, 20 can be provided with the same folding configuration and folded concurrently with each other. The distal and proximal portions 18, 20 can also be provided with the different folding configuration and folded sequentially. The circumferential bulge portion 22 can also be folded with a separate folding configuration from each of the distal and proximal portions 18, 20. Further, the circumferential bulge portion 22 can be folded in a separate folding step that occurs at a different time than folding of the distal and proximal portions 18, 20. The following folding methods described with reference to FIGS. 4-15 explain some folding configurations that are possible for the distal, proximal and circumferential bulge portions 18, 20, 22.

FIG. 4 illustrates an end view of the balloon catheter 10 shown in FIGS. 1-3 with a first plurality of folding members 36a-c spaced around the distal portion 18. Each of the folding members 36a-c includes a balloon fold surface 37. The folding members 36a-c are moved in the radial direction R into engagement with the distal portion 18. A vacuum pressure condition can be applied to the distal portion 18 while the folding members 36a-c make contact with the distal portion 18. Typically, a plurality of balloon folds 32 are created in the space defined between the surfaces 37 of each of the folding members 36a-c. The balloon folds 32 shown in FIG. 4 can be referred to as a standard wing folding arrangement or wing folds.

Figure 6:
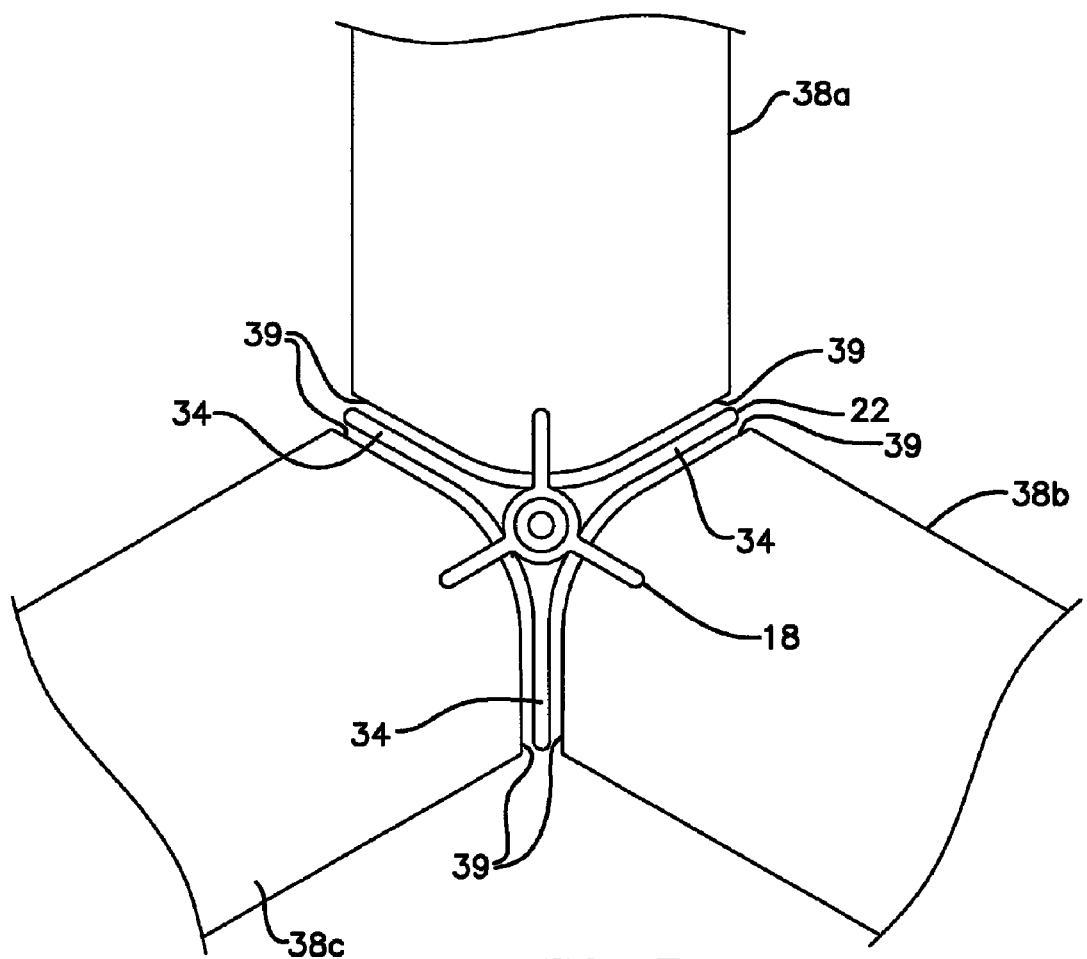
FIG. 6 is a schematic front view of the balloon catheter shown in FIG. 2 with a second set of folding members arranged to compress the circumferential bulge portion of the balloon.

After creation of the balloon folds 32, a second plurality of folding members 38a-c can be brought into engagement with the circumferential bulge portion 22 as shown in FIG. 6. Each of the folding members 38a-c includes a balloon fold surface 39. Engagement of the folding members 38a-c with the circumferential bulge portion 22 creates a plurality of balloon folds 34 in the space defined between the surfaces 39.

Figure 7:
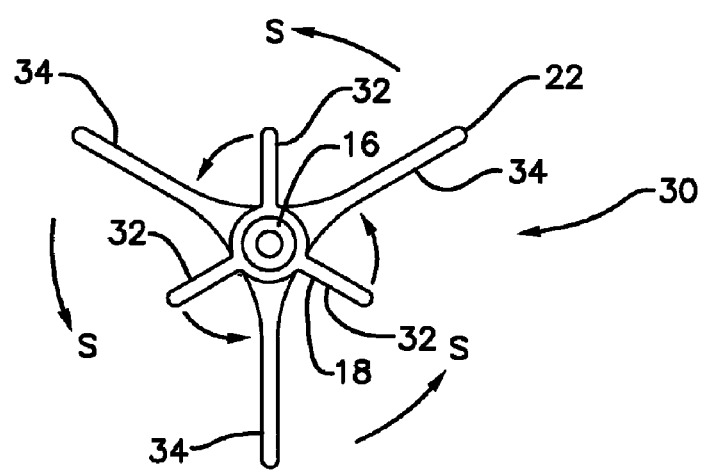
FIG. 7 is a schematic front view of the balloon catheter shown in FIG. 6 with the distal portion of the balloon compressed into three wing folds and the second set of folding members having compressed the circumferential bulge portion into three wing folds.

A resulting folded balloon arrangement 30 is shown in FIG. 7. A similar set of folding steps to those described for folding of the proximal or circumferential bulge portions 18, 22 can be used to create balloon folds in the proximal portion 20. Folding of the proximal portion 20 can be performed concurrently with folding of the distal portion 18 or the circumferential bulge portion 22.

After creation of the fold arrangement 30 shown in FIG. 7, the balloon folds 32, 34 can be wrapped in the rotation direction S about the guidewire housing 16. In some arrangements, the balloon folds 32, 34 can be rotated in opposite directions. In still further arrangements, the folds 32, 34 can be compressed in a non-uniform pattern such as by applying a radially directed inward force to compress all of the folds 32, 34 toward the guidewire housing 16.

Figure 8:
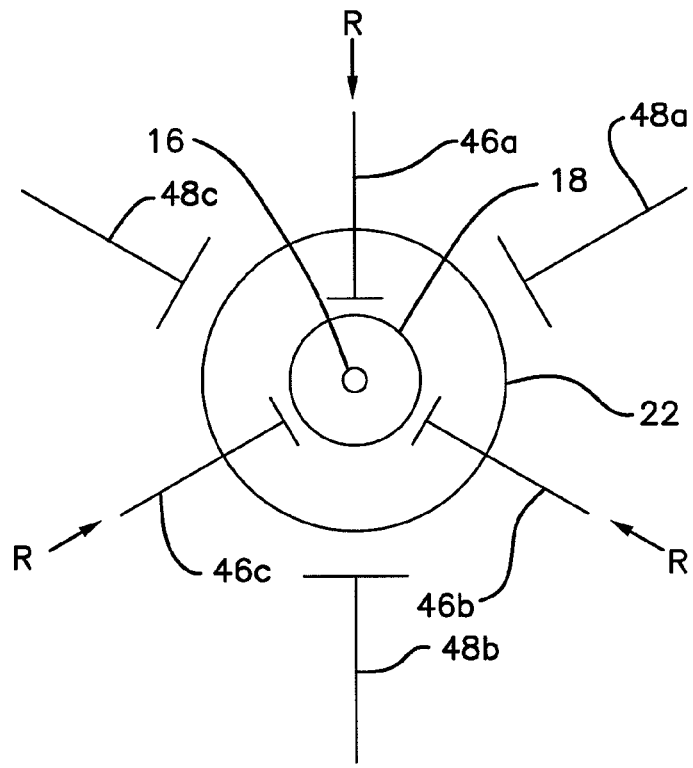
FIG. 8 is a schematic front view of the balloon catheter shown in FIG. 2 with folding members arranged to compress a distal portion of the balloon and a circumferential bulge portion of the balloon into either U-shaped or T-shaped folds.
Figure 8A:
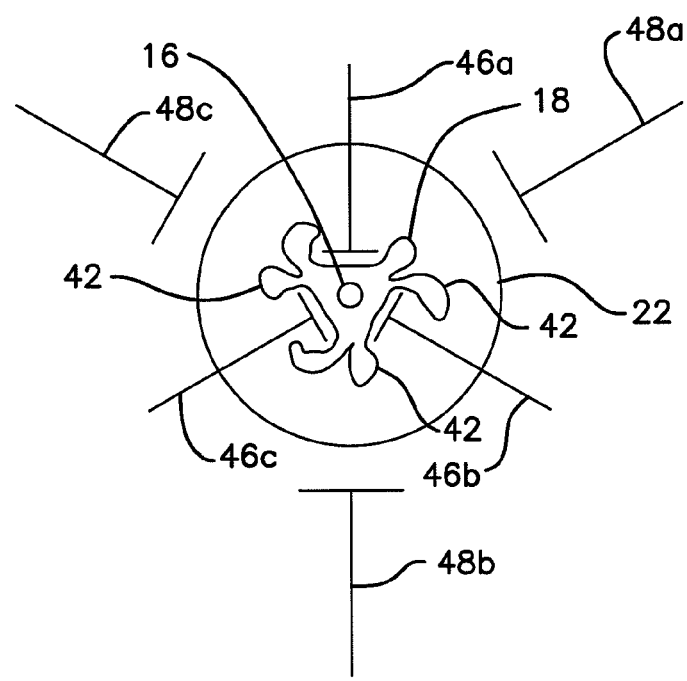
FIG. 8A is a schematic front view of the balloon catheter shown in FIG. 8 with a first set of the folding members arranged in engagement with the distal portion of the balloon.

Another folding configuration is now described with reference to FIGS. 8-10. In FIG. 8, the balloon member 12 is shown from the end view with a plurality of T-shaped folding members 46a-c arranged around a periphery of the distal portion 18. The distal portion 18 is folded by moving the folding members 46a-c in the direction R into engagement with the distal portion 18. With the folding members 46a-c in engagement with the distal portion 18 (i.e., move radially inward in the direction R until engagement with the guidewire housing 16), a vacuum pressure condition can be applied to the distal portion 18 thereby wrapping the distal portion 18 around the T-shaped end of the folding members 46a-c to create three U-shaped folds (see FIG. 8A).

In an alternative arrangement, an additional folding step can be used to help form the U-shaped fold into a T-shaped fold. An additional set of folding members (not shown) having a flat surface are moved into engagement with those parts of the distal portion 18 extending around the folding members 46a-c. These additional folding members tend to flatten the folds of distal portion 18 into T-shaped balloon folds.

A second plurality of T-shaped folding members 48a-c can be moved in the direction R into engagement with the circumferential bulge portion 22 as shown in FIG. 9 to create three addition sets of U-shaped folds 44. One or more of the U-shaped folds 44 can be formed into a T-shaped fold by engaging an additional set of folding members (not shown) with the balloon folds 44 while the folding members 48a-c remain engaged with the circumferential bulge portion 22.

After creation of the two sets of U-shaped balloon folds 42, 44 shown in FIG. 10 (or T-shaped folds as discussed above), the balloon folds 42, 44 can be compressed toward the guidewire housing 16 to minimize the outer profile of the balloon member 12. A radially inward directed force in the direction R can be applied to the balloon folds 42, 44 to compress the balloon 12. Alternatively, a rotational force, for example in the direction S, can be applied to the balloon folds 42, 44.

Referring now to FIG. 11, the balloon member 12 is shown in an alternative fold arrangement in an end view of the balloon member 12. At least one of the distal and circumferential bulge portions 18, 22 includes a C-shaped fold 54. The C-shaped fold for at least of the portions 18, 22 can be compressed against the guidewire housing 16 by application of a force in the direction R.

FIGS. 4-11 illustrate just three of the many different balloon fold configurations that are possible for each of the distal, proximal, and circumferential bulge portions 18, 20, 22. The various balloon fold configurations can be mixed and matched among the different balloon portions 18, 20, 22.

FIGS. 12 and 13 illustrate an alternative folding arrangement for the circumferential bulge portion 22. In FIG. 12, a force P in the proximal direction and a force D in the distal direction are applied to opposing distal and proximal sides, respectively, of the circumferential bulge portion 22. The circumferential bulge portion 22 is compressed into a plurality of balloon folds 66 that are arranged in a plane generally parallel to a longitudinal dimension of the balloon member 12. The folds 64 can also be referred to as axially arranged folds. The folding arrangement shown in FIGS. 12 and 13 for the circumferential bulge portion 22 can be referred to an accordion folding arrangement 60. In some arrangements, only one of the distal or proximal directed forces P, D may be necessary as one or the other of the proximal or distal facing surfaces 21, 23 of the circumferential bulge portion 22 is maintained against a fixed surface while a force is applied to the opposing surface in the axial direction.

After formation of the axially arranged folds 64, an axially directed force A can be applied to one or more of the plurality of folds 64 to reduce the outer profile of the balloon member 12. The folding arrangement 60 can be used in combination with various folding techniques that are used to fold the distal and proximal portions 18, 20.

Figure 14:
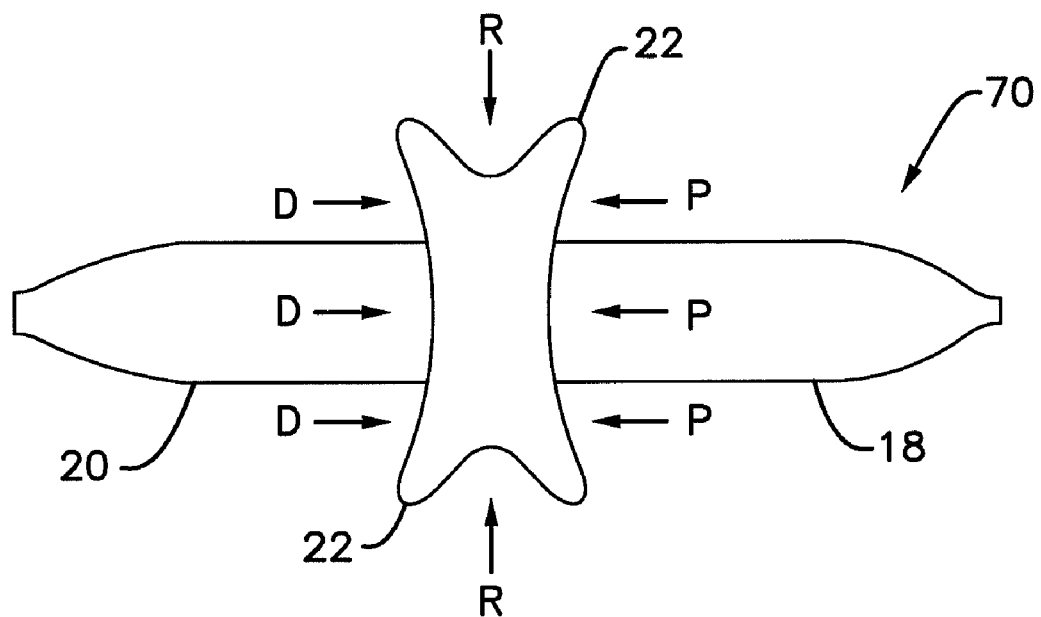
FIG. 14 is a schematic side view of the balloon catheter shown in FIG. 2 with the circumferential bulge portion having an axially and radially applied compression force being applied.
Figure 15:
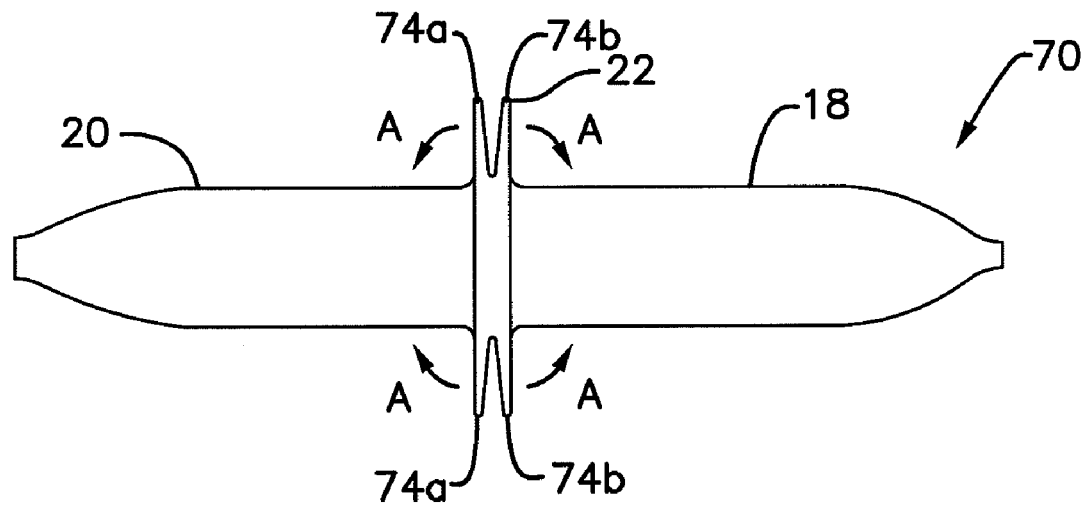
FIG. 15 is a schematic side view of the balloon catheter shown in FIG. 14 with the circumferential bulge portion compressed both axially and radially into a plurality of parallel arranged folds.

FIGS. 14 and 15 illustrate a yet further folding configuration for the circumferential bulge portion 22. In FIG. 14, a radially directed force R is applied to the circumferential bulge portion 22 while axially directed forces D, P are applied in the axial direction. The resulting accordion fold arrangement 70 includes a pair of folds 74a, 74b. The balloon folds 74a, 74b can be moved in the axial direction upon application of an axial directed force to reduce an outer profile of the circumferential bulge portion 22. As with the other balloon folding configurations described herein, the accordion fold arrangement 70 can be used in combination with any of the other balloon fold configurations that are used to fold the distal and proximal portions 18, 20.

The circumferential bulge portion 22 can be compressed axially as described with reference to FIGS. 12-15 even if the distal and proximal ends of the balloon are fixed axially because of the extra material of the balloon 12 in the axial direction needed to permit inflation of the balloon. The total length of material of the balloon 12 in the axial direction when inflated, in part because of the presence of the circumferential bulge portion 22, is greater than the length from the proximal attachment point to the distal attachment point of the balloon 12 to the catheter shaft 14 and guidewire housing 16, respectively. When the balloon 12 is in a deflated state, the circumferential bulge portion 22 can be compressed axially.

The different balloon folding configurations used for the circumferential bulge portion 22 as compared to one or both of the distal and proximal portions 18, 20 can provide expansion characteristics when using the balloon member 12 for expansion of portions of a stent as described below with reference to FIG. 16, or for expanding portions of a vessel without a stent positioned between the vessel and the balloon member 12. Some balloon folding configurations can help reduce rotation of the balloon catheter 10 relative to a stent that has already been expanded into engagement with a vessel at a vessel bifurcation. The balloon folding configurations can also minimize axial movement of the balloon catheter 10 relative to the vessel or deployed stent.

Further folding arrangements and constructions and related folding apparatuses for creating balloon folds are described in U.S. Published Application No. 2004/0215227, which is incorporated herein by reference.

An example method of treating a vessel bifurcation 90 is now shown and described with reference to FIG. 16 using balloon catheter 10 described above and the stent 80 shown in FIG. 17.

Although alternative methods are possible, one example method begins by advancing a guidewire 98 to a vessel bifurcation 70 to a position within a main vessel 92 at a location distal of an opening or ostium 96 into a branch vessel 94. A stent positioning catheter 2 (not shown) carrying a stent 80 is advanced over the guidewire 98 to the vessel bifurcation 90. The stent 80 includes a distal open end 86, a proximal open end 88, a low density strut arrangement 85, and a high density strut arrangement 83 (see FIGS. 16-17). An example stent 180 having high and low density strut arrangements 83, 85, and distal and proximal open ends 86, 88 is shown in FIG. 18. The stent positioning catheter is adjusted in the axial direction until the high density strut arrangement 83 is positioned in axial alignment with the opening 96 into the branch vessels 94.

The low density strut arrangement 85 can include a plurality of struts that are spaced apart axially a greater distance than the axial spacing of the high density strut arrangement 83. Further, the high density strut arrangement 83 can include at least one strut member that has a length when the strut is in a fully expanded state that is longer than a fully expanded length of the struts of the low density strut arrangement 85. The high density strut arrangement 83 can also include fewer connecting points between adjacent struts as compared to the number of connecting points between struts of the low density strut arrangement 85.

A balloon member of the stent positioning catheter is then inflated to expand the stent 90 into engagement with the main vessel 92. The balloon member is then deflated and the stent positioning catheter is retracted proximally along the guidewire 98 out of the patient. The balloon catheter 10 is advanced over the guidewire 98 to the vessel bifurcation 90 until the circumferential bulge portion 22 of the balloon member 12 is arranged in axial alignment with the opening 96 into the branch vessel 94. A marker 15 (see FIG. 1) or other feature of the balloon catheter 10 can be used to help the operator visually determine the relative position between the circumferential bulge portion 22 and the opening 96 of the branch vessel 94.

Figure 16:
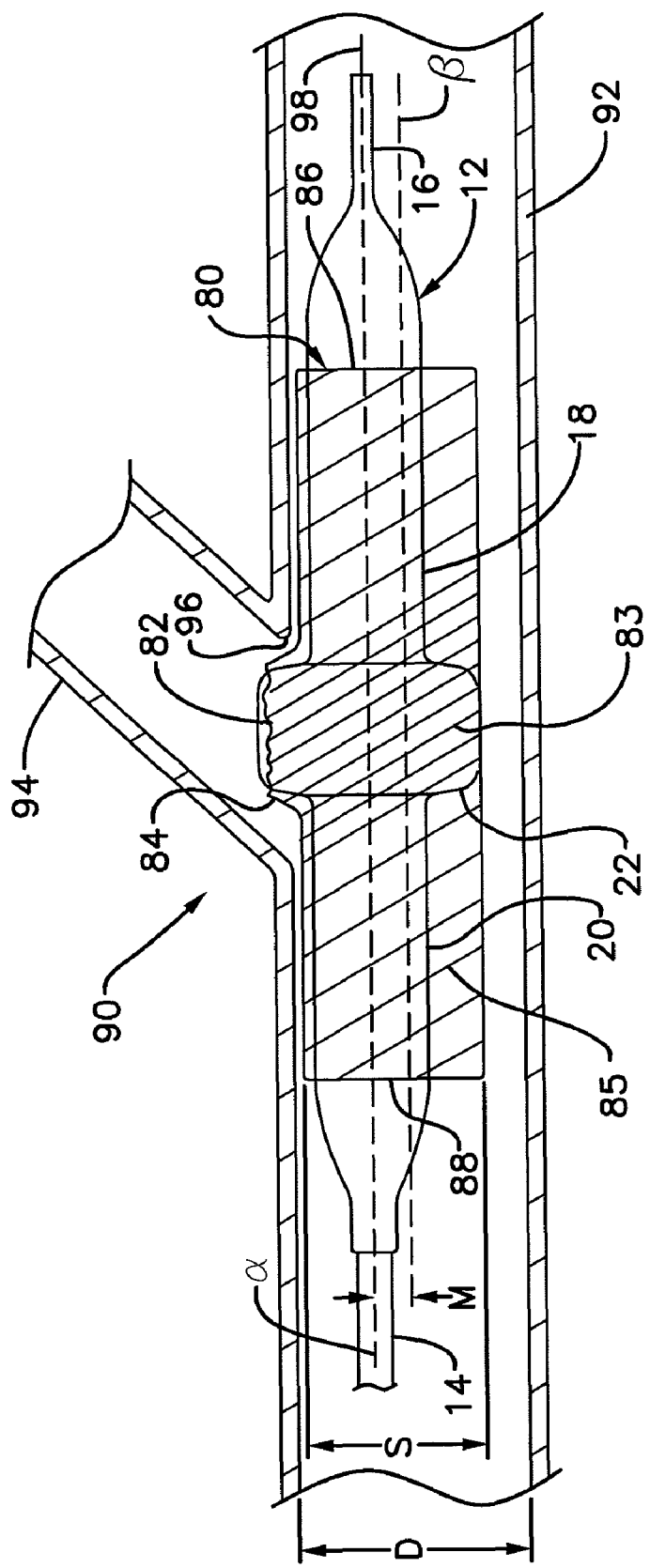
FIG. 16 is a schematic side view of the balloon catheter shown in FIG. 2 in position to expand a portion of a pre-dilated stent at a vessel bifurcation.

The balloon member 12 is then inflated as shown in FIG. 16. The inflated circumferential bulge portion 22 engages against an interior of the stent 80 at a location on the main vessel wall opposite the opening 96 into the branch vessel 94, thereby shifting the balloon catheter 10 radially away from a center line β of the main vessel 72 to a position where a central axis a of the catheter assembly 300 is spaced a distance M from axis β (see FIG. 16). The maximum radial size of the distal and proximal portions 18, 20 is less than the internal minimum dimension D of the vessel 92 so that no further expansion of the stent in the area distal and proximal of the opening 96 occurs.

The circumferential bulge portion 22 in the inflated state shown in FIG. 16 has a portion thereof that engages the high density strut arrangement 83 of stent 80 to move a portion of the stent 80 in a radial outward direction into the branch vessel 94. FIG. 16 illustrates a portion 84 of the stent 80 that extends in a radial outward direction through the opening 96 into the branch vessel 94. As this portion 84 extends in the radial outward direction, a side opening 82 can be defined in the stent between adjacent strut members that have been extended into the branch vessel 94. The side opening 82 can be used as an opening through which additional devices can be advanced for further treatment of the branch vessel 94. Further opening of the side opening 82 by moving the struts into engagement with the branch vessel wall can provide a less obstructed pathway for blood flow to move from the main vessel 92 into the branch vessel 94.

The balloon member 12 can then be deflated and the balloon catheter 10 can be removed proximally from the patient. In a further treatment step, a branch guidewire can be advanced through the side opening 82 and into the branch vessel 74, followed by advancement of another post dilatation balloon catheter over the branch guidewire and through the side opening 82. A balloon member of this post dilatation balloon catheter can be inflated to further expand the side opening 82 and move the portion 84 into further engagement with the branch vessel 94 in the area of the opening 96. In a still further treatment step, a secondary stent can be advanced through the side opening 82 and into the branch vessel 94 with a portion of a secondary stent overlapping with the portion 84 of stent 80. The secondary stent can be expanded into engagement with the portion 84 and portions of the branch vessel 94 for treatment of the vessel bifurcation 90.

Many other treatment methods and additional or varied steps from those described with reference to FIG. 16 can be used. Furthermore, many balloon catheter arrangements are possible that can result in creation of a circumferential bulge portion in the balloon member that is used to expand a portion of an already expanded stent in a post-dilatation procedure such as the method described above with reference to FIG. 16. Any of the features described with reference to FIGS. 1-16 can be combined in any desired combination to provide alternative arrangements and treatment methods within the scope of the present disclosure.

Materials and Other Considerations

The term "transparent" as used herein for purposes of describing a portion of a side catheter branch is defined as a structure through which a visual indicator of the main catheter branch can be identified by an assembler. A transparent structure typically has properties of transmitting light without appreciable scattering so that bodies lying beyond the side catheter branch are visible. Alternatively, the term "transparent" can be defined as a structure that is fine or sheer enough to be seen through. The term "transparent" as it applies to the side catheter branch features disclosed herein can be at least partially translucent in which a certain amount of light is able to pass through the side catheter branch so that objects beyond the translucent structure, while not clearly seen, can be seen well enough to identify the visual indicator on the main catheter branch to provide the assembler the ability to properly align the side balloon with the lateral branch opening of the stent. In some cases, visibility of the assembler can be enhanced with the use of magnifying equipment such as a magnifying glass or a microscope, thermal equipment, or emissive equipment depending on the properties of the visual indicator on the main catheter branch.

A wide variety of stents, catheters, and guidewire configurations can be used with the catheter assembly embodiments of the present disclosure. The inventive principles disclosed herein should not be limited to any particular design or configuration. Some example stents that can be used with the catheter assemblies disclosed herein can be found in, for example, U.S. Pat. Nos. 6,210,429, 6,325,826, 6,706,062, 7,220,275, and U.S. Published Patent Application No. 2004/0176837 titled SELF-EXPANDING STENT AND CATHETER ASSEMBLY AND METHOD FOR TREATING BIFURCATIONS, the entire contents of which are incorporated herein by reference. In general, the aforementioned stents include a lateral branch opening located between distal and proximal open ends of the stent. The lateral branch opening defines a path between an inner lumen or inner volume of the stent and an area outside of the stent. The stent lateral branch opening is distinct from the cell openings defined between strut structures from which the stent sidewall is constructed. In some stents, the lateral branch opening can be surrounded by expandable structure. The expandable structure can be configured to extend radially into the branch lumen of the bifurcation upon expansion of, for example, an inflatable portion of the bifurcation treatment system. Typically, the stent is expanded after being positioned in the main lumen with the lateral branch opening aligned with an opening into the branch lumen. Alignment of the lateral branch opening with the opening into the branch lumen includes both radial and axial alignment. The stent, including the expandable structure surrounding the lateral branch opening, can be expanded with a single expansion or multiple expansions using one or more inflatable members.

The main and side balloons, and all other balloons disclosed herein, can be made of any suitable balloon material including compliant and non-compliant materials and combinations thereof. Some example materials for the balloons and catheters disclosed herein include thermoplastic polymers, polyethylene (high density, low density, intermediate density, linear low density), various copolymers and blends of polyethylene, ionomers, polyesters, polycarbonates, polyamides, poly-vinyl chloride, acrylonitrile-butadiene-styrene copolymers, polyether-polyester copolymers, and polyether-polyamide copolymers. One suitable material is Surlyn®, a copolymer polyolefin material (DuPont de Nemours, Wilmington, Del.). Still further suitable materials include thermoplastic polymers and thermoset polymeric materials, poly (ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

The balloon catheter 10 can include marker material that is visible under X-ray or in fluoroscopy procedures. For example, the marker material can be more easily identified and distinguished under X-ray or in fluoroscopy procedures. Some example marker materials include gold, platinum and tungsten. In one embodiment, the marker material can be included in a band structure that is secured to any portion of the balloon member 12, shaft 14, or guidewire housing 16. In other embodiments, the marker material is part of the material composition of portions of the balloon catheter 10. Viewability of features of the balloon catheter 10 under X-ray or fluoroscopy can assist a physician operating the balloon catheter 10 to more easily adjust a position of the balloon catheter 10 relative to the vessel bifurcation 90. Example markers and marker materials suitable for use with assembly 10 are described in, for example, U.S. Pat. No. 6,692,483 to Vardi, et al., and co-pending U.S. Published Patent Application No. 2007/0203562, filed on Feb. 22, 2007, and titled MARKER ARRANGEMENT FOR BIFURCATION CATHETER, which matters are incorporated herein by reference.

One aspect of the present disclosure relates to a method of folding a balloon member, wherein the balloon member includes a proximal portion, a distal portion, and a circumferential bulge portion. The circumferential bulge portion is positioned at a location between the proximal and distal portions of the balloon and extends around a circumference of the balloon member. The circumferential bulge portion has a maximum inflated dimension that is greater than a maximum radially outward expanded dimension of the proximal portion of the balloon and a maximum radially outward expanded dimension of the distal portion of the balloon member. The method includes folding at least one of the proximal and distal portions of the balloon member, and folding the circumferential bulge portion of the balloon member in a step separate from folding the at least one of the proximal and distal portions.

Another aspect of the present disclosure relates to a folded post dilatation balloon catheter. The catheter includes a balloon member having a distal portion, a proximal portion, and a circumferential bulge portion. The circumferential bulge portion is positioned at a location between the proximal and distal portions of the balloon and extends around a circumference of the balloon member. The circumferential bulge portion has a maximum dimension when inflated that is greater than a maximum dimension of the proximal portion and a maximum dimension of the distal portion when the proximal and distal portions are inflated. The circumferential bulge portion has a fold configuration when in a deflated state that is different from a fold configuration of at least one of the distal portion and the proximal portion when the proximal and distal portions are in a deflated state.

It is noted that not all of the features characterized herein need to be incorporated within a given arrangement, for the arrangement to include improvements according to the present disclosure.

We claim:

1. A method of folding a balloon member, the balloon member having a proximal portion that is substantially cylindrical when inflated, a distal portion that is substantially cylindrical when inflated, and a circumferential bulge portion, the circumferential bulge portion being positioned at a location between the proximal and distal portions of the balloon, the circumferential bulge portion extending around a circumference of the balloon member and having a maximum inflated dimension that is greater than a maximum radially outward expanded dimension of the proximal portion of the balloon and a maximum radially outward expanded dimension of the distal portion of the balloon member, the method comprising:
   (a) folding at least one of the proximal and distal portions of the balloon member by moving a plurality of separate folding members in a radial direction into contact with the at least one of the proximal and distal portions; and
   (b) folding the circumferential bulge portion of the balloon member in a step separate from folding the at least one of the proximal and distal portions; wherein the step of folding at least one of the proximal and distal portions results in a different fold configuration from a fold configuration resulting from the step of folding the circumferential bulge portion.

2. The method of claim 1, further comprising inflating the balloon member before the steps of folding at least one of the proximal and distal portions and folding the circumferential bulge portion.

3. The method of claim 1, further comprising applying a vacuum pressure condition within the balloon member during the steps of folding at least one of the proximal and distal portions and folding the circumferential bulge portion.

4. The method of claim 1, wherein the step of folding at least one of the proximal and distal portions includes creating a wing fold configuration that has at least one balloon fold arranged in a plane arranged parallel with and extending through a longitudinal axis of the balloon member.

5. The method of claim 1, wherein the step of folding the at least one of the proximal and distal portions includes creating a fold configuration having one of a T-shaped fold, a C-shaped fold or a U-shaped fold.

6. The method of claim 1, wherein the step of folding the at least one of the proximal and distal portions includes creating at least three folds in each of the proximal and distal portions.

7. The method of claim 1, wherein the step of folding the circumferential bulge portion includes creating a wing fold configuration that has at least one balloon fold arranged in a plane arranged parallel with and extending through a longitudinal axis of the balloon member.

8. The method of claim 1, wherein the step of folding the circumferential bulge portion includes creating a fold configuration having one of a T-shaped fold, a C-shaped fold or a U-shaped fold.

9. The method of claim 1, wherein the step of folding the circumferential bulge portion includes creating a C-shaped fold configuration.

10. The method of claim 1, wherein the step of folding the circumferential bulge portion includes creating at least three folds in each of the proximal and distal portions.

11. The method of claim 1, wherein the step of folding the at least one of the proximal and distal portions occurs before the step of folding the circumferential bulge portion.

12. The method of claim 1, wherein the step of folding the at least one of the proximal and distal portions occurs after the step of folding the circumferential bulge portion.

13. The method of claim 1, further comprising reducing an outer profile of the folded at least one of the proximal and distal portions and the folded circumferential bulge portion.

14. The method of claim 1, wherein the proximal and distal portions are folded simultaneously and before the step of folding the circumferential bulge portion.

15. A method of folding a balloon member, the balloon member having a proximal portion that is substantially cylindrical when inflated, a distal portion that is substantially cylindrical when inflated, and a circumferential bulge portion, the circumferential bulge portion being positioned at a location between the proximal and distal portions of the balloon, the circumferential bulge portion extending around a circumference of the balloon member and having a maximum inflated dimension that is greater than a maximum radially outward expanded dimension of the proximal portion of the balloon and a maximum radially outward expanded dimension of the distal portion of the balloon member, the method comprising:
   folding the proximal, distal, and circumferential bulge portions of the balloon member simultaneously by moving a plurality of separate folding members in a radial direction into contact with each of the proximal, distal, and circumferential portions, wherein the folding step results in separate fold configurations in each of the proximal, distal, and circumferential bulge portions, wherein the fold configurations in the proximal and distal portions are different from the fold configuration in the circumferential bulge portion.

* * * * *